(12) United States Patent
Ujita et al.

(10) Patent No.: US 8,097,746 B2
(45) Date of Patent: Jan. 17, 2012

(54) METHOD FOR PRODUCING 2-ISOPROPENYL-5-METHYL-4-HEXEN-1-YL 3-METHYL-2-BUTENOATE

(75) Inventors: Katsuji Ujita, Tainai (JP); Junko Sato, Tainai (JP); Takashi Fukumoto, Tainai (JP)

(73) Assignee: Kuraray Co., Ltd., Kurashiki-shi, Okayama (JP)

( * ) Notice: Subject to any disclaimer, the term of this patent is extended or adjusted under 35 U.S.C. 154(b) by 353 days.

(21) Appl. No.: 11/910,860

(22) PCT Filed: Mar. 29, 2006

(86) PCT No.: PCT/JP2006/306460
§ 371 (c)(1),
(2), (4) Date: Nov. 26, 2007

(87) PCT Pub. No.: WO2006/109570
PCT Pub. Date: Oct. 19, 2006

(65) Prior Publication Data
US 2009/0023941 A1    Jan. 22, 2009

(30) Foreign Application Priority Data

Apr. 5, 2005 (JP) ................................. 2005-108699

(51) Int. Cl.
*C07C 309/67* (2006.01)
*C07C 67/00* (2006.01)
(52) U.S. Cl. .......................................... 558/55; 560/225
(58) Field of Classification Search .................... 558/55; 560/225
See application file for complete search history.

(56) References Cited

U.S. PATENT DOCUMENTS 3,666,789 A * 5/1972 Itaya et al. .................... 560/124

FOREIGN PATENT DOCUMENTS

| GB | 1 244 188 A | | 8/1971 |
| GB | 1244188 | * | 8/1971 |
| GB | 2 189 244 A | | 10/1987 |
| JP | 62-249943 A | | 10/1987 |

OTHER PUBLICATIONS

Hartung et al. "A radical version of the bromine cyclization of alkenols" C. R. Acad. Sci. Paris, Chimie, 2001, pp. 649-666.*
Carey et al. Advanced Organic Chemistry, Fourth Edition, Part B: Reactions and Synthesis, 2002, 147-150.*
Millar et al., *J. Econ. Entomol.*, 95(4): 706-714 (2002).
Hartung et al., *C.R. Acad. Sci. Paris, Chimie/Chemistry*, 4(7): 649-666 (2001).
Zada et al., *Tetrahedron: Asymmetry*, 15(15): 2339-2343 (2004).

* cited by examiner

*Primary Examiner* — Joseph Kosack
(74) *Attorney, Agent, or Firm* — Leydig, Voit & Mayer, Ltd.

(57) ABSTRACT

The present invention provides a method of producing 2-isopropenyl-5-methyl-4-hexen-1-yl 3-methyl-2-butenoate industrially advantageously in a high yield. More particularly, the present invention provides a method of producing 2-isopropenyl-5-methyl-4-hexen-1-yl 3-methyl-2-butenoate represented by the following formula (IV):

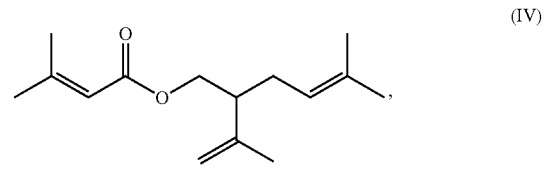

(IV)

which comprises reacting 2-isopropenyl-5-methyl-4-hexen-1-ol with an organic sulfonyl halide in the presence of a basic substance to give a sulfonate compound represented by the following formula (III):

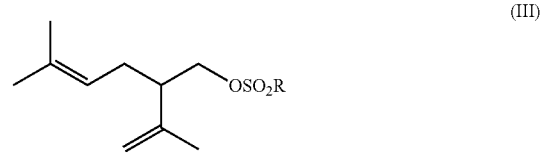

(III)

wherein R is a hydrocarbon group, and reacting the obtained sulfonate compound with senecionic acid in the presence of a basic substance.

4 Claims, No Drawings

METHOD FOR PRODUCING 2-ISOPROPENYL-5-METHYL-4-HEXEN-1-YL 3-METHYL-2-BUTENOATE

TECHNICAL FIELD

The present invention relates to a method of producing 2-isopropenyl-5-methyl-4-hexen-1-yl 3-methyl-2-butenoate represented by the following formula (IV):

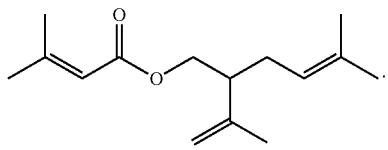
(IV)

The 2-isopropenyl-5-methyl-4-hexen-1-yl 3-methyl-2-butenoate obtained by the present invention is useful as an insect pheromone used for controlling insect pest of grape.

BACKGROUND ART

Conventionally, as a method of producing 2-isopropenyl-5-methyl-4-hexen-1-yl 3-methyl-2-butenoate, a method comprising reacting senecioyl chloride with 2-isopropenyl-5-methyl-4-hexen-1-ol represented by the following formula (I):

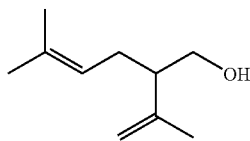
(I)

in the presence of a basic substance has been known (see, patent reference 1 and non-patent reference 1).
[patent reference 1] GB-B-1,244,188 (see p. 2, Example 2)
[non-patent reference 1] Tetrahedron Letters, 2001, vol. 42, p. 1619-1621 (see Scheme 1)

DISCLOSURE OF THE INVENTION

Problems to be Solved by the Invention

The present inventors have reproduced the methods of the above-mentioned patent reference 1 and non-patent reference 1 and encountered the problem of generation of corrosive acidic gas during production of senecioyl chloride, and the problem of the decomposition of the resultant product, 2-isopropenyl-5-methyl-4-hexen-1-yl 3-methyl-2-butenoate, during distillation purification due to the influence of by-produced impurity, which in turn causes a low yield of about 65%. Accordingly, it has been clarified that the methods are not industrially advantageous production methods.

Hence, the object of the present invention is to provide a method capable of producing 2-isopropenyl-5-methyl-4-hexen-1-yl 3-methyl-2-butenoate industrially advantageously in a high yield.

Means of Solving the Problems

According to the present invention, the above-mentioned object can be achieved by providing a method of producing 2-isopropenyl-5-methyl-4-hexen-1-yl 3-methyl-2-butenoate, which comprises reacting 2-isopropenyl-5-methyl-4-hexen-1-ol represented by the following formula (I):

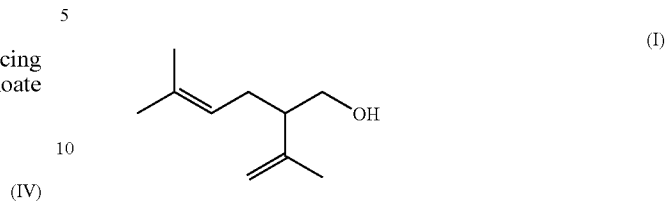
(I)

with an organic sulfonyl halide represented by the following formula (II):

$$RSO_2X \quad (II)$$

wherein R is a hydrocarbon group and X is a halogen atom [hereinafter to be referred to as organic sulfonyl halide (II)], in the presence of a basic substance to give a sulfonate compound represented by the following formula (III):

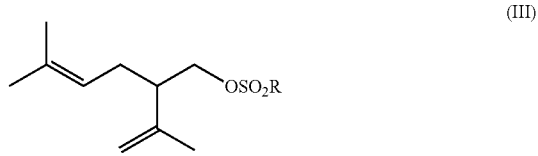
(III)

wherein R is as defined above [hereinafter to be referred to as sulfonate compound (III)], and reacting the obtained sulfonate compound (III) with senecionic acid in the presence of a basic substance.

Effect of the Invention

According to the present invention, 2-isopropenyl-5-methyl-4-hexen-1-yl 3-methyl-2-butenoate useful as an insect pheromone used for controlling insect pest of grape can be industrially advantageously produced in a high yield.

BEST MODE FOR EMBODYING THE INVENTION

In the formula, as the hydrocarbon group for R, for example, an alkyl group such as methyl group, ethyl group, n-propyl group, isopropyl group, n-butyl group, s-butyl group, t-butyl group and the like; an aromatic hydrocarbon group such as phenyl group, o-tolyl group, m-tolyl group, p-tolyl group and the like; and the like can be mentioned. As the halogen atom for X, chlorine atom, bromine atom, iodine atom and the like can be mentioned.

Specific examples of organic sulfonyl halide (II) include methanesulfonyl chloride, p-toluenesulfonyl chloride and the like.

In the following, the step for obtaining sulfonate compound (III) by reacting 2-isopropenyl-5-methyl-4-hexen-1-ol with organic sulfonyl halide (II) in the presence of a basic substance (hereinafter to be referred to as the first step) is explained.

As the basic substance to be used in the first step, for example, an organic amine such as triethylamine, tributylamine and the like; a nitrogen-containing heterocyclic aromatic compound such as pyridine and the like; an alkali metal carbonate or alkaline earth metal carbonate such as sodium carbonate, potassium carbonate, calcium carbonate, lithium carbonate and the like; an alkali metal hydride such as sodium hydride and the like; an alkali metal alkoxide such as sodium methoxide, sodium ethoxide and the like and the like can be mentioned. Of these, triethylamine is preferably used. The amount of the basic substance to be used is preferably within the range of 1-10 mol, more preferably within the range of 1-3 mol, per 1 mol of 2-isopropenyl-5-methyl-4-hexen-1-ol.

The amount of the organic sulfonyl halide (II) to be used is preferably within the range of 0.7-10 mol, more preferably within the range of 1-3 mol, per 1 mol of 2-isopropenyl-5-methyl-4-hexen-1-ol.

The first step is preferably performed in the presence of a solvent. The solvent to be used is not particularly limited as long as it does not adversely influence the reaction and, for example, an aromatic hydrocarbon such as toluene, xylene, mesitylene and the like; an aliphatic hydrocarbon such as hexane, heptane, octane and the like; an ether such as diethylether, diisopropyl ether and the like; a halogenated hydrocarbon such as dichloromethane, carbon tetrachloride and the like; an amide such as N,N-dimethylformamide, N-methylpyrrolidone and the like; and the like can be mentioned. These solvents may be used alone or in a mixture of two or more kinds thereof. While the amount of the solvent to be used is not particularly limited, it is generally preferably within the range of 0.5-100 mass, more preferably 1-10 mass, per 1 mass of 2-isopropenyl-5-methyl-4-hexen-1-ol.

The reaction temperature is preferably within the range of −20° C. to 100° C., more preferably 0° C. to 50° C. When it exceeds 100° C., sulfonate compound (III) tends to be decomposed and, when it is less than −20° C., the reaction becomes unpreferably slow. While the reaction pressure is not particularly limited, the reaction is conveniently and preferably performed under normal pressure. While the reaction time varies depending on the kinds, amount of use and the like of 2-isopropenyl-5-methyl-4-hexen-1-ol, a basic substance, organic sulfonyl halide (II) and a solvent, it is generally within the range of 5 min -24 hr.

The first step can be carried out, for example, by adding organic sulfonyl halide (II) to a mixed solution of 2-isopropenyl-5-methyl-4-hexen-1-ol, a basic substance and a solvent, and stirring at a given temperature for a given time.

The sulfonate compound (III) can be isolated from the reaction mixture obtained by the above-mentioned method and purified by a method generally used for the isolation and purification of organic compounds. For example, water is added to the reaction mixture, the mixture is extracted with an organic solvent such as an ester such as methyl acetate, ethyl acetate, butyl acetate and the like; an aromatic hydrocarbon such as toluene and the like; an aliphatic hydrocarbon such as hexane, heptane and the like; a halogenated hydrocarbon such as dichloromethane and the like; an ether such as diethyl ether, diisopropyl ether and the like; and the like, and the obtained extract is concentrated and purified by distillation, silica gel column chromatography and the like, whereby sulfonate compound (III) can be obtained at a high purity. The sulfonate compound (III) obtained in the first step can also be used in the next step (the below-mentioned second step) without isolation from the reaction mixture and purification.

Next, the step of obtaining 2-isopropenyl-5-methyl-4-hexen-1-yl 3-methyl-2-butenoate by reacting sulfonate compound (III) with senecionic acid in the presence of a basic substance (hereinafter to be referred to as the second step) is explained.

As the basic substance to be used in the second step, those similar to the basic substances used in the first step can be mentioned. Of these, an alkali metal carbonate or alkaline earth metal carbonate such as sodium carbonate, potassium carbonate, calcium carbonate, lithium carbonate and the like, or an alkali metal hydride such as sodium hydride and the like is preferably used. They may be used in the form of aqueous solution where necessary. The amount of the basic substance to be used is preferably within the range of 0.5-10 mol, more preferably within the range of 0.7-3 mol, per 1 mol of sulfonate compound (III).

When the above-mentioned basic substance is used in the form of an aqueous solution, a phase-transfer catalyst may be further added as necessary in the second step. As the phase-transfer catalyst to be used, for example, tetrabutylammonium chloride, tetrabutylammonium bromide, tetrabutylammonium sulfate, trimethylstearylammonium chloride, trimethylstearylammonium bromide, trioctylmethylammonium chloride, trioctylmethylammonium bromide, benzyltrimethylammonium chloride and the like can be mentioned. When a phase-transfer catalyst is added, the amount thereof to be added is preferably within the range of 0.1-30 mass, more preferably within the range of 0.5-10 mass, per 100 mass of sulfonate compound (III).

The amount of senecionic acid to be used is preferably within the range of 1-10 mol, more preferably within the range of 1-3 mol, per 1 mol of sulfonate compound (III).

The second step is preferably performed in the presence of a solvent. The solvent to be used is not particularly limited as long as it does not adversely influence the reaction and, for example, aliphatic hydrocarbon such as hexane, heptane, octane and the like; aromatic hydrocarbon such as toluene, xylene, mesitylene and the like; ether such as diisopropyl ether, tetrahydrofuran, dioxane and the like; amide such as N,N-dimethylformamide, N-methylpyrrolidone and the like; and the like can be mentioned. They may be used alone or in a mixture of two or more kinds thereof. While the amount of the solvent to be used is not particularly limited, generally, it is preferably within the range of 1-100 mass, more preferably within the range of 1-10 mass, per 1 mass of sulfonyl compound (III).

The reaction temperature is preferably within the range of 50° C. to 180° C., more preferably 80° C. to 150° C. When it exceeds 180° C., 2-isopropenyl-5-methyl-4-hexen-1-yl 3-methyl-2-butenoate tends to decompose in addition to sulfonate compound (III) and, when it is lower than 50° C., the reaction becomes unpreferably slow. While the reaction pressure is not particularly limited, the reaction is conveniently and preferably performed under normal pressure. The reaction time varies depending on the kinds, amount of use and the like of sulfonate compound (III), a basic substance, senecionic acid and a solvent. It is generally within the range of 10 min -50 hr.

The second step can be performed by, for example, (1) a method comprising mixing a basic substance, sulfonate compound (III), senecionic acid, a solvent and, where necessary, a phase-transfer catalyst, and stirring the mixture at a given temperature for a given time, (2) a method comprising mixing a basic substance, senecionic acid, a solvent and, where necessary, a phase-transfer catalyst, adding sulfonate compound (III) dropwise while stirring the mixture at a given temperature, and stirring the mixture for a given time, (3) a method comprising mixing a basic substance, sulfonate compound (III), a solvent and, where necessary, a phase-transfer catalyst, stirring the mixture at a given temperature, adding senecionic acid to the obtained reaction mixture and stirring the mixture for a given time and the like.

The 2-isopropenyl-5-methyl-4-hexen-1-yl 3-methyl-2-butenoate can be isolated from the reaction mixture obtained by the above-mentioned method and purified by a method generally used for the isolation and purification of organic compounds. For example, water is added to the reaction mixture, the mixture is extracted with an organic solvent such as an aliphatic hydrocarbon such as hexane, heptane, octane and the like; an acetate ester such as methyl acetate, ethyl acetate, butyl acetate and the like; an aromatic hydrocarbon such as toluene and the like; an aliphatic hydrocarbon such as hexane, heptane and the like; a halogenated hydrocarbon such as dichloromethane and the like; an ether such as diethyl ether, diisopropyl ether and the like; and the like, and the obtained extract is concentrated and purified by distillation, silica gel column chromatography and the like, whereby 2-isopropenyl-5-methyl-4-hexen-1-yl 3-methyl-2-butenoate can be obtained at a high purity.

The 2-isopropenyl-5-methyl-4-hexen-1-ol used as the starting material in the present invention can be easily produced by, for example, reducing 2-isopropenyl-5-methyl-4-hexenal, which is obtained by reacting senecioyl aldehyde dimethylacetal with 3-methyl-1-buten-3-ol in the presence of an acid catalyst, with sodium borohydride (see, for example, JP-A-2002-308815).

EXAMPLES

The present invention is explained in more detail in the following by referring to Examples, which are not to be construed as limitative.

Example 1

Synthesis of 2-isopropenyl-5-methyl-4-hexen-1-yl Methanesulfonate

2-Isopropenyl-5-methyl-4-hexen-1-ol (154.25 g, 1.00 mol), toluene (775.6 g) and triethylamine (122.5 g, 1.21 mol) were charged in a four-neck flask (inner volume 2 L) equipped with a thermometer, a stirrer and a dropping funnel, and the mixture was cooled to 5° C. Then, methanesulfonyl chloride (137.5 g, 1.20 mol) was added dropwise to this mixture over 30 min. After the completion of the dropwise addition, the reaction mixture was further stirred at 25° C. for 1 hr. Water (462.4 g) was added to the obtained reaction mixture, the mixture was stirred for 15 min, and the organic layer was separated. The obtained organic layer was washed with 5 mass % aqueous solution of sodium hydrogencarbonate (488.0 g) and water (464.1 g) and concentrated to give 2-isopropenyl-5-methyl-4-hexen-1-yl methanesulfonate (237.73 g, 0.972 mol, yield 97.2%, purity 95%). The result of $^1$H-NMR measurement of 2-isopropenyl-5-methyl-4-hexen-1-yl methanesulfonate is shown below. The present compound is a novel substance.

$^1$H-NMR (300 MHz, CDCl$_3$, TMS) δ: 5.04 (1H, t), 4.90 (1H, t), 4.79 (1H, s), 4.16 (2H, d), 2.99 (3H, s), 2.47 (1H, m), 2.03-2.24 (2H, m), 1.70 (3H, s), 1.68 (3H, s), 1.60 (3H, s)

Example 2

Synthesis of 2-isopropenyl-5-methyl-4-hexen-1-yl 3-methyl-2-butenoate

Senecionic acid (108.3 g, 1.08 mol), potassium carbonate (101.7 g, 0.74 mol), tetrabutylammonium chloride (11.3 g, 0.04 mol), water (8.8 g) and toluene (742.7 g) were charged in a three-neck flask (inner volume 3 L) equipped with a condenser, a thermometer, a stirrer and a dropping funnel, and the mixture was stirred between 90 and 95° C. for 30 min. Then, a toluene solution of 2-isopropenyl-5-methyl-4-hexen-1-yl methanesulfonate obtained by the method of Example 1 (1002.1 g, containing 0.97 mol of 2-isopropenyl-5-methyl-4-hexen-1-yl methanesulfonate) was added dropwise to this mixture over 10 hr. After the completion of the dropwise addition, the reaction mixture was further stirred between 90 and 95° C. for 6 hr. Water (677.3 g) was added to the obtained reaction mixture, the mixture was stirred for 15 min, and the organic layer was separated. The obtained organic layer was further washed with water (451.8 g) and concentrated, and the obtained residue was distilled under reduced pressure to give 2-isopropenyl-5-methyl-4-hexen-1-yl 3-methyl-2-butenoate (209.9 g, 0.863 mol, yield 89.0%, purity 97.2%). The result of $^1$H-NMR measurement of 2-isopropenyl-5-methyl-4-hexen-1-yl 3-methyl-2-butenoate is shown below.

$^1$H-NMR (300 MHz, CDCl$_3$, TMS) δ: 5.66 (1H, s), 5.07 (1H, t), 4.82 (1H, t), 4.75 (1H, s), 4.07 (2H, d), 2.42 (1H, m), 2.15 (3H, s), 2.03-2.24 (2H, m), 1.88 (3H, s), 1.70 (3H, s), 1.68 (3H, s), 1.60 (3H, s)

Example 3

Synthesis of 2-isopropenyl-5-methyl-4-hexen-1-yl 3-methyl-2-butenoate

A toluene solution of 2-isopropenyl-5-methyl-4-hexen-1-yl methanesulfonate obtained by the method of Example 1 (60.7 g, containing 0.06 mol of 2-isopropenyl-5-methyl-4-hexen-1-yl methanesulfonate), potassium carbonate (6.23 g, 0.045 mol), tetrabutylammonium chloride (0.70 g, 2.5 mmol) and water (0.55 g) were charged in a three-neck flask (inner volume 200 mL) equipped with a condenser, a thermometer, a stirrer and a dropping funnel, and the mixture was heated between 90 and 95° C. Then, a solution of senecionic acid (6.7 g, 0.066 mol) in toluene (20 g) was added dropwise to this mixture over 1.5 hr. After the completion of the dropwise addition, the reaction mixture was further stirred between 90 and 95° C. for 8 hr. Water (42.3 g) was added to the obtained reaction mixture, the mixture was stirred for 15 min, and the organic layer was separated. The obtained organic layer was further washed with water (27.0 g) and concentrated to give 2-isopropenyl-5-methyl-4-hexen-1-yl 3-methyl-2-butenoate (14.44 g, 0.054 mol, yield 89.9%).

Example 4

Synthesis of 2-isopropenyl-5-methyl-4-hexen-1-yl 3-methyl-2-butenoate

A toluene solution of 2-isopropenyl-5-methyl-4-hexen-1-yl methanesulfonate obtained by the method of Example 1 (987.2 g, containing 1.00 mol of 2-isopropenyl-5-methyl-4-hexen-1-yl methanesulfonate), senecionic acid (111.4 g, 1.11 mol), potassium carbonate (104.2 g, 0.75 mol), tetrabutylammonium chloride (11.6 g, 0.042 mol) and water (9.1 g) were charged in a three-neck flask (inner volume 2 L) equipped with a condenser, a thermometer and a stirrer, and the mixture was stirred between 90 and 95° C. for 10 hr. Water (680.4 g) was added to the obtained reaction mixture, the mixture was stirred for 15 min, and the organic layer was separated. The obtained organic layer was further washed with water (464.3 g) and concentrated, and the residue was distilled under reduced pressure to give 2-isopropenyl-5-methyl-4-hexen-1-yl 3-methyl-2-butenoate (205.73 g, 0.84 mol, yield 84.0%, purity 96.5%).

Example 5

Synthesis of 2-isopropenyl-5-methyl-4-hexen-1-yl 3-methyl-2-butenoate

2-Isopropenyl-5-methyl-4-hexen-1-yl methanesulfonate obtained by the method of Example 1 (8.01 g, 0.03 mol), senecionic acid (3.29 g, 0.033 mol), sodium carbonate (3.84 g, 0.036 mol), tetrabutylammonium chloride (0.35 g, 1.3 mmol) and toluene (124.0 g) were charged in a three-neck flask (inner volume 200 mL) equipped with a condenser, a thermometer and a stirrer, and the mixture was stirred at 112° C. for 5 hr. Water (50.0 g) was added to the obtained reaction mixture, the mixture was stirred for 15 min, and the organic layer was separated. The obtained organic layer was further washed with water (50.8 g) and concentrated to give 2-isopropenyl-5-methyl-4-hexen-1-yl 3-methyl-2-butenoate (8.61 g, 0.026 mol, yield 85.6%).

Example 6

Synthesis of 2-isopropenyl-5-methyl-4-hexen-1-yl 3-methyl-2-butenoate

2-Isopropenyl-5-methyl-4-hexen-1-yl methanesulfonate obtained by the method of Example 1 (8.06 g, 0.03 mol), senecionic acid (3.30 g, 0.033 mol), sodium carbonate (3.50 g, 0.033 mol), tetrabutylammonium bromide (0.35 g, 1.1 mmol) and toluene (123.6 g) were charged in a three-neck flask (inner volume 200 mL) equipped with a condenser, a thermometer and a stirrer, and the mixture was stirred at 112° C. for 4 hr. Water (50.0 g) was added to the obtained reaction mixture, the mixture was stirred for 15 min, and the organic layer was separated. The obtained organic layer was further washed with water (50.0 g) and concentrated to give 2-isopropenyl-5-methyl-4-hexen-1-yl 3-methyl-2-butenoate (9.11 g, 0.025 mol, yield 83.6%).

Example 7

Synthesis of 2-isopropenyl-5-methyl-4-hexen-1-yl 3-methyl-2-butenoate

2-Isopropenyl-5-methyl-4-hexen-1-yl methanesulfonate obtained by the method of Example 1 (0.27 g, corresponding to 1 mmol of 2-isopropenyl-5-methyl-4-hexen-1-yl methanesulfonate), senecionic acid (0.11 g, 1.1 mol), sodium carbonate (0.12 g, 1.1 mol) and N,N-dimethylformamide (5 g) were charged in a three-neck flask (inner volume 50 mL) equipped with a condenser, a thermometer and a stirrer, and the mixture was stirred at 120° C. for 3 hr. The solvent was evaporated from the obtained reaction mixture, toluene (20.0 g) and water (20.0 g) were added to the residue, the mixture was stirred, and the organic layer was separated. The separated organic layer was concentrated to give 2-isopropenyl-5-methyl-4-hexen-1-yl 3-methyl-2-butenoate (0.24 g, 0.819 mmol, yield 81.9%).

Example 8

Synthesis of 2-isopropenyl-5-methyl-4-hexen-1-yl 3-methyl-2-butenoate

2-Isopropenyl-5-methyl-4-hexen-1-ol (5 g, 32.41 mmol), toluene (25 g) and triethylamine (4.19 g, 41.48 mmol) were charged in a three-neck flask (inner volume 100 mL) equipped with a thermometer, a stirrer and a dropping funnel, and the mixture was cooled to 5° C. Then, p-toluenesulfonyl chloride (7.90 g, 41.48 mmol) was added, and the mixture was stirred at 50° C. for 16 hr. Water (15 g) was added to the obtained reaction mixture, the mixture was stirred for 15 min, and the organic layer was separated. The obtained organic layer was washed sequentially with 5 mass % aqueous solution of sodium hydrogencarbonate (15 g) and water (15 g) to give a toluene solution (34.10 g) containing 2-isopropenyl-5-methyl-4-hexen-1-yl p-toluenesulfonate. As a result of the GC analysis, this solution contained 2-isopropenyl-5-methyl-4-hexen-1-yl p-toluenesulfonate (9.60 g, 31.17 mmol, yield 96.2%).

Senecionic acid (3.07 g, 30.69 mmol), potassium carbonate (2.89 g, 20.93 mmol), tetrabutylammonium chloride (0.43 g, 1.54 mmol), water (0.25 g) and toluene (25 g) were charged in a three-neck flask (inner volume 200 mL) equipped with a condenser, a thermometer, a stirrer and a dropping funnel, and the mixture was stirred between 90 and 95° C. for 30 min. Then, a toluene solution (30.0 g) of 2-isopropenyl-5-methyl-4-hexen-1-yl p-toluenesulfonate (corresponding to 27.90 mmol of 2-isopropenyl-5-methyl-4-hexen-1-yl p-toluenesulfonate) obtained in the above-mentioned was added dropwise to this mixture over 1 hr. After the completion of the dropwise addition, the mixture was further stirred between 90 and 95° C. for 20 hr. Water (25.8 g) was added to the obtained reaction mixture, the mixture was stirred for 15 min, and the organic layer was separated. The obtained organic layer was further washed with water (17.2 g) and concentrated, and the obtained residue was distilled under reduced pressure to give 2-isopropenyl-5-methyl-4-hexen-1-yl 3-methyl-2-butenoate (5.70 g, 23.40 mmol, yield 83.9%, purity 97.0%).

The invention claimed is:

1. A method of producing 2-isopropenyl-5-methyl-4-hexen-1-yl 3-methyl-2-butenoate represented by the following formula (IV):

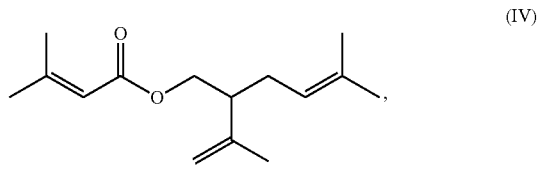

(IV)

which comprises reacting 2-isopropenyl-5-methyl-4-hexen-1-ol represented by the following formula (I):

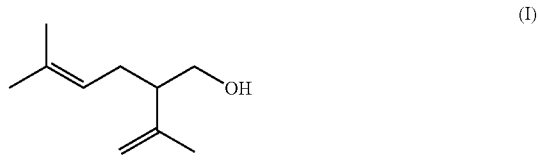

(I)

with an organic sulfonyl halide represented by the following formula (II):

$RSO_2X$ (II)

wherein R is a hydrocarbon group and X is a halogen atom, in the presence of a basic substance to give a sulfonate compound represented by the following formula (III):

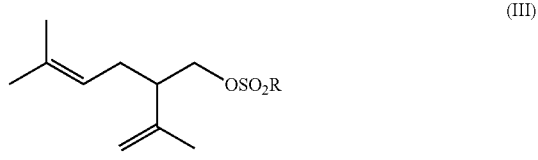

(III)

wherein R is as defined above, and reacting the obtained sulfonate compound with senecionic acid in the presence of sodium carbonate or potassium carbonate and a phase-transfer catalyst.

2. A method of producing 2-isopropenyl-5-methyl-4-hexen-1-yl 3-methyl-2-butenoate represented by the following formula (IV):

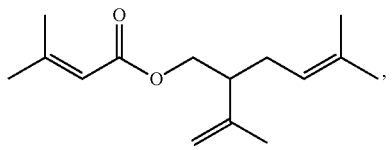
(IV)

which comprises reacting a sulfonate compound represented by the following formula (III):

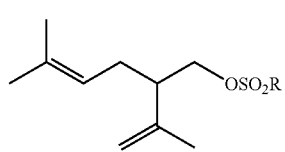
(III)

wherein R is a hydrocarbon group, with senecionic acid in the presence of sodium carbonate or potassium carbonate and a phase-transfer catalyst.

3. The method of claim 1, wherein R is an alkyl group.
4. The method of claim 2, wherein R is an alkyl group.

* * * * *